United States Patent [19]
Felix

[11] 4,336,062
[45] Jun. 22, 1982

[54] HERBICIDAL CYCLOHEXENONE DERIVATIVES
[75] Inventor: Raymond A. Felix, El Cerrito, Calif.
[73] Assignee: Stauffer Chemical Company, Westport, Conn.
[21] Appl. No.: 906,495
[22] Filed: May 16, 1978

Related U.S. Application Data
[63] Continuation-in-part of Ser. No. 834,090, Sep. 19, 1977, abandoned.
[51] Int. Cl.³ .................... A01N 31/00; A01N 37/00; A01N 37/44; A01N 37/18; A01N 47/30; C07C 83/10; C07C 155/03; C07C 149/40; C07C 125/06; C07C 103/19; C07C 103/127; C07C 103/133; C07C 127/19
[52] U.S. Cl. .......................................... 71/98; 71/100; 71/111; 71/118; 71/120; 260/453 RW; 260/455 A; 560/9; 560/27; 564/49; 564/52; 564/190; 564/207; 564/219; 564/221
[58] Field of Search ........... 71/120, 98; 260/453 RW, 260/553 A, 562 A; 560/9, 27; 564/49, 52, 190, 207, 219, 221

[56] References Cited
U.S. PATENT DOCUMENTS

| | | | |
|---|---|---|---|
| 3,707,365 | 12/1972 | Kaufman et al. | 71/123 |
| 3,820,975 | 6/1974 | Poje et al. | 71/88 |
| 3,937,726 | 2/1976 | Scherer et al. | 71/120 |
| 3,976,470 | 8/1976 | Baker | 71/100 |
| 4,090,865 | 5/1978 | Baker | 71/118 |
| 4,149,874 | 4/1979 | Felix | 560/27 |
| 4,230,483 | 10/1980 | Felix | 560/27 |

FOREIGN PATENT DOCUMENTS

| | | | |
|---|---|---|---|
| 541891 | 6/1957 | Canada | 71/123 |
| 2601447 | 7/1976 | Fed. Rep. of Germany | 71/121 |
| 45-41377 | 12/1970 | Japan | 71/123 |
| 532891 | 3/1973 | Switzerland | 71/120 |

Primary Examiner—Glennon H. Hollrah
Attorney, Agent, or Firm—Joel G. Ackerman

[57] ABSTRACT

Novel compounds having the formula

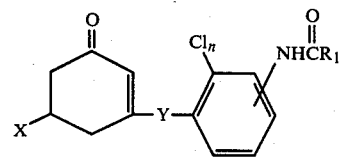

in which X is $(H)_2$ or $(CH_3)_2$; Y is oxygen or sulfur; $R_1$ is alkyl, lower alkenyl, cyclopropyl, lower alkoxy, thio-lower alkyl or

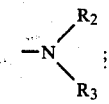

$R_2$ and $R_3$ are independently hydrogen, lower alkyl, lower alkenyl, or lower alkoxy and n is 0 or 1. The compounds have been found to possess herbicidal activity.

69 Claims, No Drawings

HERBICIDAL CYCLOHEXENONE DERIVATIVES

CROSS-REFERENCE TO RELATED APPLICATIONS

This is a continuation-in-part application of Ser. No. 834,090 filed Sept. 19, 1977, now abandoned.

DESCRIPTION OF THE INVENTION

This application relates to novel cyclohexenone derivatives and their use as herbicides. More particularly, this invention relates to new compounds having the formula

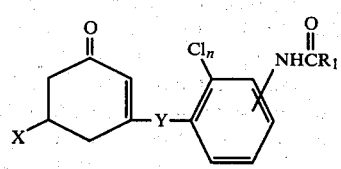

in which X is $(H)_2$ or $(CH_3)_2$; Y is oxygen or sulfur; $R_1$ is alkyl, lower alkenyl, cyclopropyl, lower alkoxy, thio-lower alkyl or

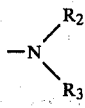

$R_2$ and $R_3$ are independently hydrogen, lower alkyl, lower alkenyl or lower alkoxy; and n is 0 or 1, provided that when n is 0 and the aminocarbonyl

group and the ether or sulfide linkage are in the para position with respect to each other, $R_1$ is cyclopropyl or 1,1-dimethylbutyl.

By the term "alkyl" is meant such groups having from 1 to 10, preferably from 1 to 6 and most preferably from 2 to 6, carbon atoms. Illustrative of said alkyl groups are methyl, ethyl, n-propyl, isopropyl, sec.-butyl and 1,1-dimethylbutyl. By the terms "lower alkyl", "lower alkoxy" and "thio-lower alkyl" are meant such groups having from 1 to 4 carbon atoms, such as methyl, ethyl, n-propyl, isopropyl, methoxy, ethoxy, thio-ethyl and the like. The term "lower alkenyl" includes such groups having from 2 to 4 carbon atoms and containing one olefinically unsaturated bond. Most preferred among lower alkenyl groups, for the compounds of this invention, are those having 3 carbon atoms, such as allyl, propenyl and isopropenyl.

The compounds of this group include both amides and ureas, depending on the nature of the $R_1$ constituent of the molecule. If $R_1$ is alkyl, lower alkenyl, cyclopropyl, lower alkoxy or thio-lower alkyl, the compounds are derivatives of carboxylic acids or thio analogs thereof, i.e. the compounds are amides, carbanilates or thiocarbanilates. If $R_1$ is a group of the formula

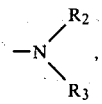

the compounds are ureas. For purposes of convenience, the group

will be generally referred to herein as the "aminocarbonyl" group.

In one embodiment, n is 0 and the aminocarbonyl group is substituted on the phenyl ring in the meta position with respect to the ether linkage. In another embodiment, n is 1 and the aminocarbonyl group is substituted on the phenyl ring in the para position with respect to the ether linkage. In a third embodiment n is 0, the aminocarbonyl group is substituted on the phenyl ring in the para position with respect to the ether linkage and $R_1$ is either cyclopropyl or 1,1-dimethylbutyl.

In one preferred embodiment, $R_1$ is

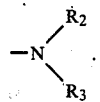

In another preferred embodiment, $R_1$ is alkyl, lower alkenyl, or cyclopropyl. Preferably, Y is oxygen.

The compounds of this invention have been found to be active herbicides; that is, the compounds have been found to be herbicidally active against various species of weeds. Weeds in the broadest sense, are plants which grow in locations in which they are not desired. For the most part, as will be seen from the data which follow, the compounds are more active as post-emergence herbicides than as pre-emergence herbicides, though some of the compounds showed at least moderately good pre-emergence herbicidal activity. The compounds have been found to generally affect broadleaf (dicotyledonous) weeds to a greater extent than grasses (monocotyledons). Some compounds in this group also exhibit activity as fungicides.

These novel compounds may be employed as both general and selective herbicides. When employed at high rates, they can be used as total weed killers, for example on railroad trackbeds, shoulders and median strips of highways, vacant lots, etc. When used at lower rates, the compounds may be satisfactory as selective herbicides; several of these compounds have been found to show good control of broadleaf weeds in corn and grain sorghum crops without seriously injuring the crops, when applied as post-emergence herbicides.

Thus, this invention also relates to a method for controlling undesirable vegetation comprising applying to the vegetation or the locus thereof an herbicidally effective amount of a compound as above described, and also relates to herbicidal compositions of matter comprising an herbicidally effective amount of a compound as described herein, plus an inert diluent or carrier suitable for use with herbicides.

An herbicide as used herein, means a compound which controls or modifies the growth of plants. By the term "herbicidally effective amount" is meant an amount of compound which causes a modifying effect upon the growth of plants. By "plants" is meant germinant seeds, emerging seedlings and established vegetation, including the roots and above-ground portions. Such modifying effects include all deviations from natural development, for example, killing, retardation, defoliation, desiccation, regulation, stunting, tillering, stimulation, leaf burn, dwarfing, and the like.

In general, the compounds of the present invention can be prepared by reacting the appropriate 3-chloro-cyclohexenone with the sodium salt of an aminophenol or an aminothiophenol to produce an aniline derivative, which is then reacted with an acyl chloride, chlorothioformate, chloroformate or carbamyl chloride in the presence of a hydrogen chloride acceptor such as triethyl amine or caustic to give the titled compounds:

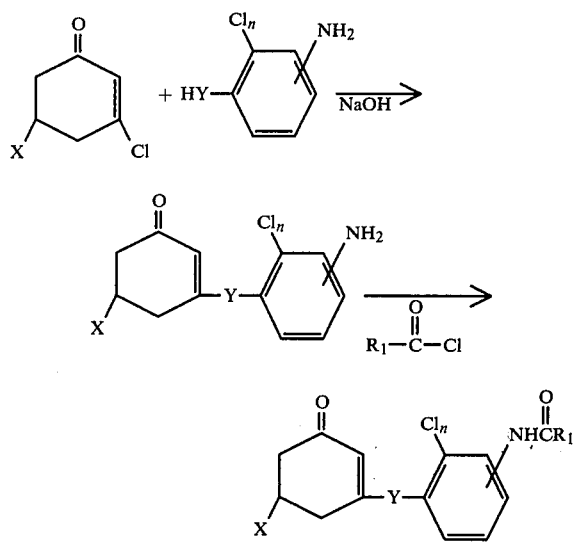

Alternatively, the ureas in particular can be prepared by reacting the appropriate 3-chloro-cyclohexenone with a hydroxyphenyl or thiophenyl urea:

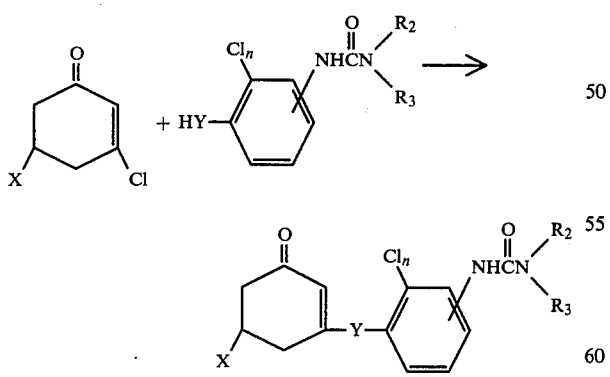

in the presence of a hydrogen chloride acceptor. X, Y, R, $R_1$, $R_2$ and $R_3$ are as previously defined. This reaction as well as the reaction between the cyclohexenone and aminophenol or aminothiophenol described above can be advantageously effected with the aid of a phase transfer catalyst such as a quaternary onium salt. Some suitable phase transfer catalysts are described in U.S. Pat. No. 3,992,432 of Starks, et al.

The following are examples of the preparation of compounds of the present invention:

EXAMPLE 1

Preparation of 5,5-dimethyl-3-(3-cyclopropionamidophenoxy)-2-cyclohexenone (Compound 3 herein)

In a one-liter flask there were placed 50 g. (0.03 mole) 5,5-dimethyl-3-chloro-2-cyclohexenone and 3 g. tetrabutyl phosphonium chloride in 150 ml. benzene. This solution was heated to reflux with vigorous stirring and a solution of 38 g. (0.35 mole) 3-aminophenol and 30 g. (0.37 mole) 50% NaOH in 60 ml. water was added dropwise over a one-hour period. The resulting mixture was then refluxed for 3 more hours. The solution was poured into 500 ml. water and extracted with methylene chloride. The methylene chloride extract was dried and evaporated to yield 61 g. (88% theoretical yield) of 5,5-dimethyl-3-(3-aminophenoxy)-2-cyclohexenone, m.p. 129°–133° C.

2.3 g. (0.01 mole) of this compound was mixed with 2 ml. triethylamine and 1.1 g. cyclopropane carboxylic acid chloride in 200 ml. ether at 5° C. with vigorous stirring. The mixture was stirred 3 hours, and poured into 100 ml. water and extracted with ether. The extract was dried and evaporated to yield 2.2 g. of the desired product, m.p. 156°–159° C.

EXAMPLE 2

Preparation of 3-(3'-isopropylureylene phenoxy)-5,5-dimethyl-2-cyclohexenone (Compound 1 herein)

In a flask there were placed 10 g. (0.05 mole) of N-isopropyl-N'-(3-hydroxyphenyl) urea and 50 ml. tetrahydrofuran. 11 g. of a 25% solution of sodium methoxide in methanol was added. The solution was stirred for 15 minutes; then the solvents were removed under vacuum. The solid residue was dissolved in 100 ml. dimethylformamide; then 7.5 g. (0.047 mole) of 5,5-dimethyl-3-chloro-2-cyclohexenone was added, followed by heating for 4 hours on a steam bath. Two hundred ml. of benzene was then added. The benzene layer was washed with three 500 ml. portions of water, dried and evaporated. There was obtained 12.8 g. (0.04 mole) of the desired product, $n_D^{30}$ 1.5179.

EXAMPLE 3

Preparation of 3-(3'-isopropylureylenephenoxy)-2-cyclohexenone (Compound 7 herein)

In a flask were placed 1.8 g. (0.01 mole) N-isopropyl-N'-(3-hydroxyphenyl)urea, 1.3 g. (0.01 mole) 3-chloro-2-cyclohexenone, 1.0 g. (0.012 mole) 50% aqueous solution of sodium hydroxide, 0.3 g. tetrabutylphosphonium chloride, 5 ml. benzene and 2 ml. water. The mixture was refluxed for 2 hours and cooled 50 ml. methylene chloride was added and the organic layer was washed with 100 ml. water. The organic layer was then dried and evaporated to yield 2.7 g. (0.009 mole) of the desired product, $n_D^{30}$ 1.5350.

Table I contains a list of representative compounds of the present invention.

TABLE I

| Compound | X | $R_1$ | n | Y | Relative* Position | $n_D^{30}$ or m.p., °C. |
|---|---|---|---|---|---|---|
| 1 | (CH₃)₂ | —NHCH(CH₃)CH₃ | 0 | O | meta | 1.5179 |
| 2 | (CH₃)₂ | C₂H₅ | 0 | O | meta | 1.5166 |
| 3 | (CH₃)₂ | ◁ | 0 | O | meta | 156–159° C. |
| 4 | (CH₃)₂ | —N(OCH₃)(CH₃) | 0 | O | meta | 1.5275 |
| 5 | (CH₃)₂ | —C(CH₃)₂C₃H₇ | 0 | O | meta | 88–90° C. |
| 6 | (H)₂ | —C(CH₃)₂C₃H₇ | 0 | O | meta | 1.5270 |
| 7 | (H)₂ | —NHCH(CH₃)CH₃ | 0 | O | meta | 1.5350 |
| 8 | (H)₂ | C₂H₅ | 0 | O | meta | 1.5405 |
| 9 | (H)₂ | n-C₃H₇ | 0 | O | meta | 1.5395 |
| 10 | (H)₂ | sec.-C₄H₉ | 0 | O | meta | 1.5280 |
| 11 | (CH₃)₂ | n-C₃H₇ | 0 | O | meta | 1.5250 |
| 12 | (CH₃)₂ | —CH=CHCH₃ | 0 | O | meta | thick glass |
| 13 | (CH₃)₂ | —C(CH₃)=CH₂ | 0 | O | meta | thick glass |
| 14 | (CH₃)₂ | —N(CH₃)₂ | 0 | O | meta | 146–149° C. |
| 15 | (CH₃)₂ | NHCH₂—C(CH₃)=CH₂ | 0 | O | meta | thick glass |
| 16 | (CH₃)₂ | ◁ | 0 | O | para | 175–178° C. |
| 17 | (CH₃)₂ | —C(CH₃)₂C₃H₇ | 0 | O | para | 1.5021 |
| 18 | (CH₃)₂ | ◁ | 1 | O | para | 208–211° C. |
| 19 | (CH₃)₂ | —C(CH₃)₂C₃H₇ | 1 | O | para | 130–133° C. |
| 20 | (CH₃)₂ | n-C₃H₇ | 1 | O | para | 136–139° C. |
| 21 | (CH₃)₂ | i-C₃H₇ | 1 | O | para | 135–139° C. |
| 22 | (CH₃)₂ | —N(OCH₃)(CH₃) | 1 | O | para | thick glass |
| 23 | (CH₃)₂ | —N(CH₃)(CH₃) | 1 | O | para | semi-solid |
| 24 | (CH₃)₂ | —CH=CH—CH₃ | 1 | O | para | sticky solid |
| 25 | (CH₃)₂ | SC₂H₅ | 0 | O | meta | 1.5448 |
| 26 | (CH₃)₂ | OC₂H₅ | 0 | O | meta | 111–116° C. |
| 27 | (CH₃)₂ | n-C₃H₇ | 0 | S | meta | 1.5415 |
| 28 | (CH₃)₂ | ◁ | 0 | S | meta | thick glass |
| 29 | (CH₃)₂ | i-C₃H₇ | 0 | S | meta | thick glass |
| 30 | (CH₃)₂ | C₂H₅ | 0 | S | meta | thick glass |

TABLE I-continued

[Structure: cyclohexenone with X substituent, connected via Y to a benzene ring bearing Cl_n and NHCR_1 with C=O]

| Compound | X | R$_1$ | n | Y | Relative* Position | $n_D^{30}$ or m.p., °C. |
|---|---|---|---|---|---|---|
| 31 | (CH$_3$)$_2$ | —CH$_2$CH=CH$_2$ | 0 | S | meta | thick glass |

*Position of aminocarbonyl group with respect to the ether or sulfide linkage.

The compounds listed in this Table I were variously identified by infrared and/or nuclear magnetic resonance spectroscopy.

Herbicidal Screening Tests

The representative compounds in the foregoing Table I were tested as herbicides in the following manner:

A. Pre-emergence Herbicide Screening Test:

Using an analytical balance, 20 mg. of the compound to be tested was weighed out on a piece of glassine weighing paper. The paper and compound were placed in a 30 ml. wide-mouth bottle and 3 ml. of acetone containing 1% polyoxyethylene sorbitan monolaurate emulsifier was added to dissolve the compound. If the material was not soluble in acetone, another solvent such as water, alcohol or dimethylformamide (DMF) was used instead. When DMF was used, only 0.5 ml. or less was used to dissolve the compound and then another solvent was used to make the volume up to 30 ml. The 3 ml. solution was sprayed uniformly on the soil contained in a small flat 7 inches long, 5 inches wide and 2.75 inches deep, one day after planting weed seeds in the flat of soil. An atomizer was used to apply the spray using compressed air at a pressure of 5 lb./sq. in. The rate of application was 8 lb./acre (8.96 kg/hectare), and the spray volume was 143 gal./acre.

On the day preceding treatment, the flat was filled to a depth of 2 inches with loamy sand soil. Seeds of seven different weed species were planted in individual rows using one species per row across the width of the flat. The seeds were covered with soil so that they were planted at a length of 0.5 inch. The seeds used were hairy crabgrass (*Digitaria sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica junces*) and curly dock (*Rumex crispus*). Ample seeds were planted to give about 20 to 50 seedlings per row after emergence, depending on the size of the plants.

After treatment, the flats were placed in the greenhouse at a temperature of 70° to 85° F. (21° to 29.5° C.) and watered by sprinkling. Two weeks after treatment the degree of injury or control was determined by comparison with untreated check plants of the same age. The injury rating from 0 to 100% was recorded for each species as percent control with 0%. representing no injury and 100% representing complete kill.

B. Post-emergence Herbicide Screening Test:

Seeds of six plant species, including hairy crabgrass, watergrass, red oat, mustard, curly dock and pinto beans (Phaseolus vulgaris) were planted in the flats as described above for pre-emergence screening. The flats were placed in the greenhouse at 70° to 85° F. (21° to 29.5° C.) and watered daily with a sprinkler. About 10 to 14 days after planting, when the primary leaves of the bean plants were almost fully expanded and the first trifoliate leaves were just starting to form, the plants were sprayed. The spray was prepared by weighing out 20 mg. of the test compound, dissolving it in 5 ml. of acetone containing 1% polyoxyethylene sorbitan monolaurate and then adding 5 ml. of water. The solution was sprayed on the foliage using an atomizer at an air pressure of 5 lb./sq. in. The spray concentration was 0.2% and the rate was 8 lb./acre (8.96 kg/hectare). The spray volume was 476 gal./acre.

The results of these tests are known in the following Table II.

TABLE II

| Compound | Pre-emergence Control | Post-emergence Control |
|---|---|---|
| 1 | 57 | 67 |
| 2 | 21 | 45 |
| 3 | 51 | 95 |
| 4 | 76 | 100 |
| 5 | 72 | 98 |
| 6 | 0 | 96 |
| 7 | 0 | 96 |
| 8 | 0 | 82 |
| 9 | 0 | 36 |
| 10 | 34 | 58 |
| 11 | 0 | 97 |
| 12 | 0 | 98 |
| 13 | 0 | 87 |
| 14 | 68 | 100 |
| 15 | 0 | 73 |
| 16 | 17 | 25 |
| 17 | 0 | 48 |
| 18 | 14 | 56 |
| 19 | 6 | 14 |
| 20 | 7 | 19 |
| 21 | 20 | 38 |
| 22 | 51 | 77 |
| 23 | 76 | 77 |
| 24 | 9 | 28 |
| 25 | 37 | 40 |
| 26 | 50 | 49 |
| 27 | 0 | 28 |
| 28 | 0 | 37 |
| 29 | 0 | 48 |
| 30 | 0 | 73 |
| 31 | 0 | 25 |

The values given in Table II represent an average control for seven plant species in pre-emergence tests and six plant species in post-emergence tests with respect to 100% control. The results of these tests indicate that many of the compounds of this type are quite effective as post-emergence herbicides.

In practice, the compounds are formulated with an inert carrier, utilizing methods well known to those skilled in the art, thereby making them suitable for application as dusts, sprays, or drenches and the like in the form and manner required. The mixtures can be dispersed in water with the aid of a wetting agent or they can be employed in organic liquid compositions, oil and water, water-in-oil emulsions, with or without the addition of wetting, dispersing or emulsifying agents. An herbicidally effective amount depends upon the nature of the seeds or plants to be controlled and the rate of application varies from 0.5 to approximately 50 pounds per acre (0.56 to 56 kg/hectare).

The phytotoxic compositions of this invention employing an herbicidally effective amount of the compounds described herein are applied to the plants in the conventional manner. Thus, the dust and liquid compositions can be applied to the plant by the use of power-dusters, boom and hand sprayers and spray-dusters. The compositions can also be applied from airplanes as a dust or a spray. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles, since these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

What is claimed is:

1. A compound having the formula

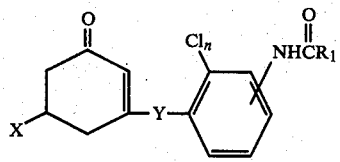

in which X is $(H)_2$ or $(CH_3)_2$, Y is oxygen or sulfur; $R_1$ is alkyl, lower alkenyl, cyclopropyl, lower alkoxy, thio-lower alkyl or

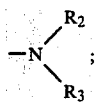

$R_2$ and $R_3$ are independently hydrogen, lower alkyl, lower alkenyl or lower alkoxy, and n is 0 or 1, provided that when n is 0 and when the aminocarbonyl group and the ether or sulfide linkage are in the para position with respect to each other, $R_1$ is cyclopropyl or 1,1-dimethylbutyl.

2. A compound according to claim 1 in which n is 0 and the aminocarbonyl group is in the meta position with respect to the ether or sulfide linkage.

3. A compound according to claim 2 in which $R_1$ is

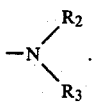

4. A compound according to claim 1 in which n is 1 and the aminocarbonyl group is in the para position with respect to the ether or sulfide linkage.

5. A compound according to claim 4 in which $R_1$ is

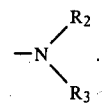

6. A compound according to claim 1 in which n is 0, the aminocarbonyl group is in the para position with respect to the ether or sulfide linkage, and $R_1$ is cyclopropyl or 1,1-dimethylbutyl.

7. A compound according to claim 1 in which X is $(H)_2$.

8. A compound according to claim 1 in which X is $(CH_3)_2$.

9. A compound according to claim 1 in which $R_1$ is alkyl.

10. A compound according to claim 9 in which $R_1$ is alkyl having from 1 to 6 carbon atoms.

11. A compound according to claim 9 in which $R_1$ is alkyl having from 2 to 6 carbon atoms.

12. A compound according to claim 9 in which $R_1$ is ethyl.

13. A compound according to claim 9 in which $R_1$ is n-propyl.

14. A compound according to claim 9 in which $R_1$ is 1,1-dimethylbutyl.

15. A compound according to claim 1 in which $R_1$ is lower alkenyl.

16. A compound according to claim 15 in which $R_1$ is propenyl.

17. A compound according to claim 15 in which $R_1$ is isopropenyl.

18. A compound according to claim 1 in which $R_1$ is

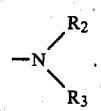

19. A compound according to claim 18 in which $R_2$ is hydrogen and $R_3$ is lower alkyl.

20. A compound according to claim 18 in which $R_2$ is lower alkoxy and $R_3$ is lower alkyl.

21. A compound according to claim 18 in which $R_2$ and $R_3$ are both lower alkyl.

22. A compound according to claim 1 in which $R_1$ is lower alkoxy.

23. A compound according to claim 1 in which $R_1$ is thio-lower alkyl.

24. A compound according to claim 1 in which Y is oxygen.

25. A compound according to claim 1 in which Y is sulfur.

26. A compound according to claim 1 in which X is $(CH_3)_2$, Y is oxygen, $R_1$ is

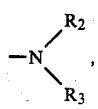

$R_2$ is hydrogen, $R_3$ is isopropyl, n is 0 and the aminocarbonyl group is in the meta position with respect to the ether linkage.

27. A compound according to claim 1 in which X is $(CH_3)_2$, Y is oxygen, $R_1$ is ethyl, n is 0 and the aminocarbonyl group is in the meta position with respect to the ether linkage.

28. A compound according to claim 1 in which X is $(CH_3)_2$, Y is oxygen, $R_1$ is cyclopropyl, n is 0 and the aminocarbonyl group is in the meta position with respect to the ether linkage.

29. A compound according to claim 1 in which X is $(CH_3)_2$, Y is oxygen, $R_1$ is

$R_2$ is methoxy, $R_3$ is methyl, n is 0 and the aminocarbonyl group is in the meta position with respect to the ether linkage.

30. A compound according to claim 1 in which X is $(CH_3)_2$, Y is oxygen, $R_1$ is 1,1-dimethylbutyl, n is 0 and the aminocarbonyl group is in the meta position with respect to the ether linkage.

31. A compound according to claim 1 in which X is $(H)_2$, Y is oxygen, $R_1$ is 1,1-dimethylbutyl, n is 0 and the aminocarbonyl group is in the meta position with respect to the ether linkage.

32. A compound according to claim 1 in which X is $(H)_2$, Y is oxygen, $R_1$ is

$R_2$ is hydrogen, $R_3$ is isopropyl, n is 0 and the aminocarbonyl group is in the meta position with respect to the ether linkage.

33. A compound according to claim 1 in which X is $(H)_2$, Y is oxygen, $R_1$ is ethyl, n is 0 and the aminocarbonyl group is in the meta position with respect to the ether linkage.

34. A compound according to claim 1 in which X is $(H)_2$, Y is oxygen, $R_1$ is n-propyl, n is 0 and the aminocarbonyl group is in the meta position with respect to the ether linkage.

35. A compound according to claim 1 in which X is $(H)_2$, Y is oxygen, $R_1$ is sec.-butyl, n is 0 and the aminocarbonyl group is in the meta position with respect to the ether linkage.

36. A compound according to claim 1 in which X is $(CH_3)_2$, Y is oxygen, $R_1$ is n-propyl, n is 0 and the aminocarbonyl group is in the meta position with respect to the ether linkage.

37. A compound according to claim 1 in which X is $(CH_3)_2$, Y is oxygen, $R_1$ is propenyl, n is 0 and the aminocarbonyl group is in the meta position with respect to the ether linkage.

38. A compound according to claim 1 in which X is $(CH_3)_2$, Y is oxygen, $R_1$ is isopropenyl, n is 0 and the aminocarbonyl group is in the meta position with respect to the ether linkage.

39. A compound according to claim 1 in which X is $(CH_3)_2$, Y is oxygen, $R_1$ is

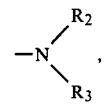

$R_2$ and $R_3$ are both methyl, n is 0 and the aminocarbonyl group is in the meta position with respect to the ether linkage.

40. A compound according to claim 1 in which X is $(CH_3)_2$, Y is oxygen, $R_1$ is

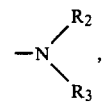

$R_2$ is hydrogen, $R_3$ is 2-methylallyl, n is 0 and the aminocarbonyl group is in the meta position with respect to the ether linkage.

41. A compound according to claim 1 in which X is $(CH_3)_2$, Y is oxygen, $R_1$ is cyclopropyl, n is 0 and the aminocarbonyl group is in the para position with respect to the ether linkage.

42. A compound according to claim 1 in which X is $(CH_3)_2$, Y is oxygen, $R_1$ is 1,1-dimethylbutyl, n is 0 and the aminocarbonyl group is in the para position with respect to the ether linkage.

43. A compound according to claim 1 in which X is $(CH_3)_2$, Y is oxygen, $R_1$ is cyclopropyl, n is 1 and the aminocarbonyl group is in the para position with respect to the ether linkage.

44. A compound according to claim 1 in which X is $(CH_3)_2$, Y is oxygen, $R_1$ is 1,1-dimethylbutyl, n is 1 and the aminocarbonyl group is in the para position with respect to the ether linkage.

45. A compound according to claim 1 in which X is $(CH_3)_2$, Y is oxygen, $R_1$ is n-propyl, n is 1 and the aminocarbonyl group is in the para position with respect to the ether linkage.

46. A compound according to claim 1 in which X is $(CH_3)_2$, Y is oxygen, $R_1$ is isopropyl, n is 1 and the aminocarbonyl group is in the para position with respect to the ether linkage.

47. A compound according to claim 1 in which X is $(CH_3)_2$, Y is oxygen, $R_1$ is

$R_2$ is methoxy, $R_3$ is methyl, n is 1 and the aminocarbonyl group is in the para position with respect to the ether linkage.

48. A compound according to claim 1 in which X is $(CH_3)_2$, Y is oxygen, $R_1$ is

$R_2$ and $R_3$ are both methyl, n is 1 and the aminocarbonyl group is in the para position with respect to the ether linkage.

49. A compound according to claim 1 in which X is (CH$_3$)$_2$, Y is oxygen, R$_1$ is propenyl, n is 1 and the aminocarbonyl group is in the para position with respect to the ether linkage.

50. A compound according to claim 1 in which X is (CH$_3$)$_2$, Y is oxygen, R$_1$ is thioethyl, n is 0 and the aminocarbonyl group is in the meta position with respect to the ether linkage.

51. A compound according to claim 1 in which X is (CH$_3$)$_2$, Y is oxygen, R$_1$ is ethoxy, n is 0 and the aminocarbonyl group is in the meta position with respect to the ether linkage.

52. A compound according to claim 1 in which X is (CH$_3$)$_2$, Y is sulfur, R$_1$ is n-propyl, n is 0 and the aminocarbonyl group is in the meta position with respect to the sulfide linkage.

53. A compound according to claim 1 in which X is (CH$_3$)$_2$, Y is sulfur, R$_1$ is cyclopropyl, n is 0 and the aminocarbonyl group is in the meta position with respect to the sulfide linkage.

54. A compound according to claim 1 in which X is (CH$_3$)$_2$, Y is sulfur, R$_1$ is isopropyl, n is 0 and the aminocarbonyl group is in the meta position with respect to the sulfide linkage.

55. A compound according to claim 1 in which X is (CH$_3$)$_2$, Y is sulfur, R$_1$ is ethyl, n is 0 and the aminocarbonyl group is in the meta position with respect to the sulfide linkage.

56. A compound according to claim 1 in which X is (CH$_3$)$_2$, Y is sulfur, R$_1$ is allyl and the aminocarbonyl group is in the meta position with respect to the sulfide linkage.

57. A method of controlling undesirable vegetation comprising applying to the vegetation or the locus thereof an herbicidally effective amount of a compound having the formula

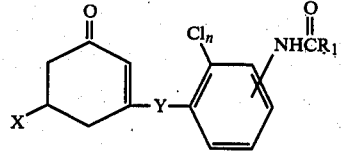

in which X is (H)$_2$ or (CH$_3$)$_2$; Y is oxygen or sulfur; R$_1$ is alkyl, lower alkenyl, cyclopropyl, lower alkoxy, thio-lower alkyl or

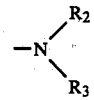

R$_2$ and R$_3$ are independently hydrogen, lower alkyl, lower alkenyl, or lower alkoxy, n is 0 or 1 provided that when n is 0 and when the aminocarbonyl group and the ether or sulfide linkage are in the para position with respect to each other, R$_1$ is cyclopropyl, or 1,1-dimethylbutyl.

58. A method according to claim 57 in which n is 0 and the aminocarbonyl group is in the meta position with respect to the ether or sulfide linkage.

59. A method according to claim 57 in which n is 1 and the aminocarbonyl group is in the para position with respect to the ether or sulfide linkage.

60. A method according to claim 57 in which n is 0, the aminocarbonyl group is in the para position with respect to the ether or sulfide linkage, and R$_1$ is cyclopropyl or 1,1-dimethylbutyl.

61. A method according to claim 57 in which R$_1$ is alkyl.

62. A method according to claim 61 in which R$_1$ is alkyl having from 1 to 6 carbon atoms.

63. A method according to claim 61 in which R$_1$ is alkyl having from 2 to 6 carbon atoms.

64. A method according to claim 57 in which R$_1$ is lower alkenyl.

65. A method according to claim 57 in which R$_1$ is

66. A method according to claim 57 in which Y is oxygen.

67. A method according to claim 57 in which the compound is applied subsequent to the emergence of the undesirable vegetation.

68. A method according to claim 67 in which the compound is applied to control broadleaf vegetation.

69. A herbicidal composition of matter comprising:
(a) an herbicidally effective amount of a compound having the formula

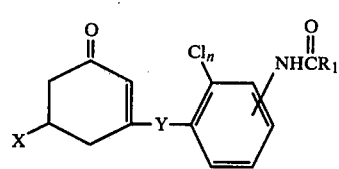

in which X is (H)$_2$ or (CH$_3$)$_2$; Y is oxygen or sulfur; R$_1$ is alkyl, lower alkenyl, cyclopropyl, lower alkoxy or thio-lower alkyl or

R$_2$ and R$_3$ are independently hydrogen, lower alkyl, lower alkenyl or lower alkoxy and n is 0 or 1, provided that when n is 0 and the aminocarbonyl group is in the para position with respect to the ether or sulfide linkage, R$_1$ is cyclopropyl or 1,1-dimethylbutyl; and
(b) a herbicidally suitable inert carrier or diluent.

* * * * *